United States Patent [19]

Edwards

[11] 4,006,746
[45] Feb. 8, 1977

[54] SURGICAL KNIFE

[76] Inventor: John Edwards, 645 Riverside Ave., Fort Wayne, Ind. 46805

[22] Filed: Apr. 28, 1975

[21] Appl. No.: 572,108

[52] U.S. Cl. .................................. 128/305; 30/293
[51] Int. Cl.² .................. A61B 17/32; B26B 29/00
[58] Field of Search .............. 128/305, 304, 303, 2; 30/289, 293

[56] References Cited

UNITED STATES PATENTS

| | | | |
|---|---|---|---|
| 1,735,271 | 11/1929 | Groff | 128/305 X |
| 2,898,906 | 8/1959 | Seiger | 128/305 X |
| 3,035,581 | 5/1962 | Bonta | 128/305 |
| 3,191,301 | 6/1965 | Rubinstein | 30/293 |
| 3,222,784 | 12/1965 | Phillips et al. | 30/293 |

FOREIGN PATENTS OR APPLICATIONS

| | | | |
|---|---|---|---|
| 2,106,001 | 8/1971 | Germany | 128/305 |

Primary Examiner—John D. Yasko

[57] ABSTRACT

This invention relates to a manual surgical knife. An elongated knife blade and an elongated blade guide are rigidly and releasably clamped in spaced apart relation. The blade guide has a guide surface which overlies and has a transverse dimension substantially greater than the blade transverse dimension. The blade guide has a flat planar guide surface which faces and is spaced from the surface of the knife blade. A guide shank is affixed to and longitudinally extends from the guide. A handle is attached to the guide shank and is laterally offset from the guide surface and inclined in a direction away from the guide surface thereby defining a hand clearance. The guide has edge-supporting ribs extending generally orthogonally from the guide in a direction opposite to the guide surface.

7 Claims, 6 Drawing Figures

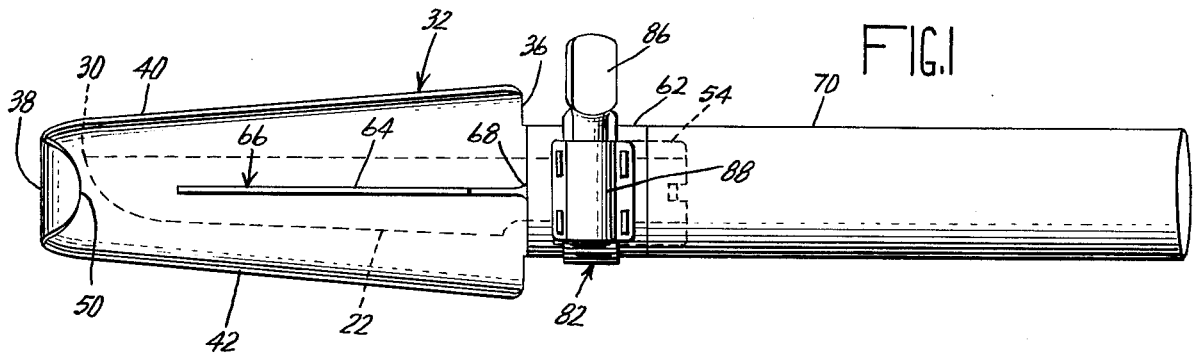
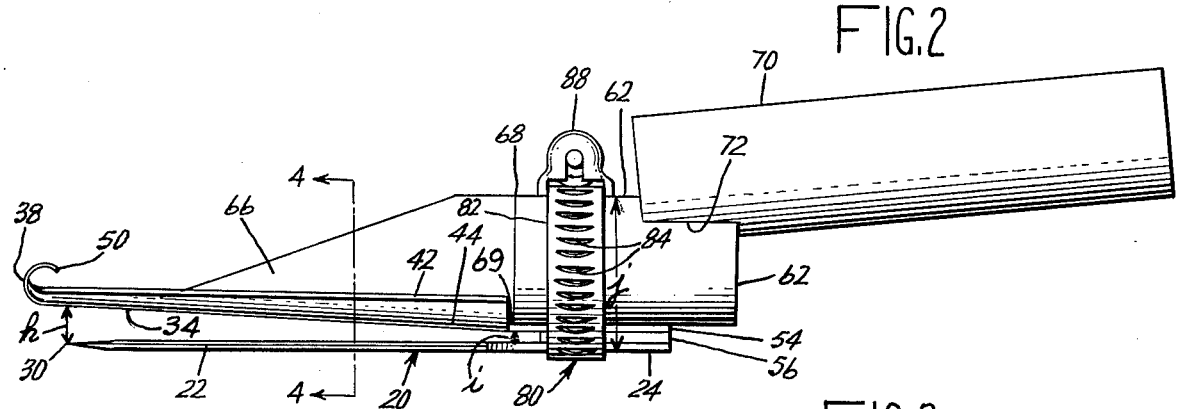
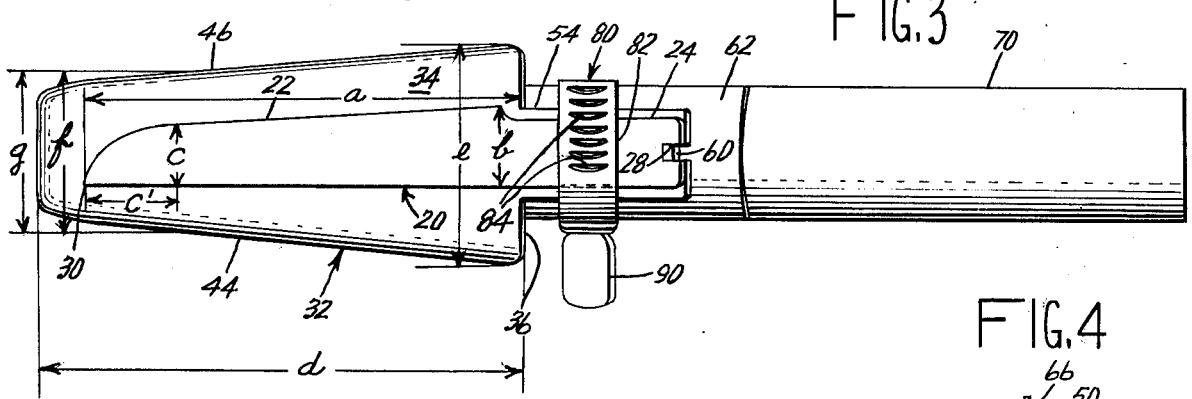
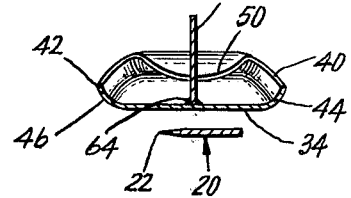
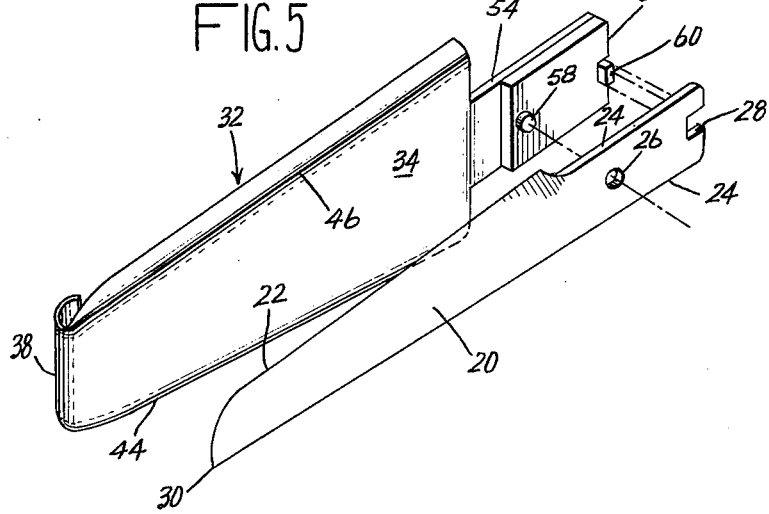

SURGICAL KNIFE

BACKGROUND OF THE INVENTION

1. Field of the Invention

This invention relates to manual surgical knives and more particularly to a knife having a blade guide for cutting skin "flaps".

2. Brief Description of the Prior Art

A mastectomy operation requires a cutting of the outer skin in such a manner that the anatomy or body matter beneath the skin is accessible to the surgeon. After completion of the operation, the skin is returned in place and rejoined. It is for the mastectomy required that the thickness of the flap be tapered such that the smaller thickness is at the outer end of the flap and the larger thickness is at the base of the flap which remains attached to the skin surface. Flaps cut in this manner provide proper nourishment to the skin during the operating and healing period to minimize skin necrosis. A prior device has utilized an elongated blade guides having a transverse dimension approximately equal to the knife blade transverse dimension thus making the blade attitude, or attack angle, and uniformity of cut difficult to visually perceive. Further, such a device has not been readily adaptable to manual cutting and hence the blade has been power driven. As a result, the control of the cutting action has been seriously diminished due to inherent loss of control in power driven equipment. Further, the bulk of this power driven instrument, the power cables and handle construction of such instrument obstruct freedom of surgical operation.

SUMMARY OF THE INVENTION

This invention provides a surgical knife assembly having an elongated knife blade. The base end of the knife blade has a longitudinally extending blade shank. A tab notch is formed at the end of the shank and a dowel hole is formed on the body of the shank, longitudinally spaced from the notch. The blade has an end distal from the base end. An elongated tapered blade guide, has a longitudinally extending guide shank at the base end thereof. A spacer plate is affixed to the guide shank and has a dowel longitudinally spaced from an end tab. The spacer plate dowel and tab are registrable with an insertable in the blade shank dowel hole and tab notch. Clamping means are provided to releasably clamp the blade against the spacer plate thereby securing the blade to the guide in spaced relation to define a cutting clearance therebetween. A guide surface overlies the blade and extends transversely on either side of the blade. The longitudinal guide edges are rounded. The guide has a distal free end which is turned backwardly on itself to provide a visual gauge of the distal blade end.

A supporting rib is formed on and extends orthogonally from the guide to provide rigidity to the guide and aid in visual measurement of the guide attitude.

A handle is affixed to the guide shank and is orthogonally offset from the guide surface and inclined upwardly away from the guide surface to uniquely provide a hand clearance for manual operation of the knife.

It is therefore an object of this invention to provide a lightweight, manual surgical knife having a guide surface for manual cutting of skin flaps.

It is an object of this invention to provide in the surgical knife of the foregoing object a blade guide overlying and having a transverse dimension on either side of the blade to facilitate manipulation of the blade, provide uniformity of surgical cut, to provide a stable relationship with respect to the surface of the skin, and provide visual measurement of the attitude of the guide and knife.

Another object of this invention is to provide in the device of the foregoing objects a handle orthogonally offset from and inclined away from the guide surface to provide a hand clearance during manual surgical operation.

The above-mentioned and other features and objects of this invention and the manner of attaining them will become more apparent and the invention itself will be best understood by reference to the following description of an embodiment of the invention taken in conjunction with the accompanying drawings.

BRIEF DESCRIPTION OF THE DRAWINGS

FIG. 1 is a top view of a preferred embodiment;
FIG. 2 is a side view of the embodiment of FIG. 1;
FIG. 3 is a bottom view of the embodiment of FIG. 1;
FIG. 4 is a section taken at 4—4 of FIG. 2;
FIG. 5 is an exploded view of the guide and knife blade; and
FIG. 6 is a section taken of the guide and knife showing a second embodiment of this invention.

BRIEF DESCRIPTION OF A PREFERRED EMBODIMENT

Referring to FIGS. 1–5, an elongated knife blade 20 has a cutting edge 22 and a shank 24 extending longitudinally from the base end thereof. Shank 24 has dowel hole 26 and tab notch 28. Blade 20 has at its distal free end a point 30.

An elongated guide 32 having a generally flat, planar guide surface 34 is generally tapered from a base edge 36 to a distal end 38. Side edges 40 and 42 are arcuately formed upwardly and away from guide surface 34 to form rounded skin contact edges 44 and 46. The distal end 38 is formed by rolling tip 50 backwardly toward base edge 36 thus forming a rounded surface for contact with the body skin.

Affixed to and extending longitudinally of edge 36 is guide shank 54 which has affixed thereto, as by welding, a spacer plate 56. A dowel 58 is formed on and extends from plate 56 and a locating tab 60 is struck from and extends from plate 56. Dowel 58 and tab 60 are registerable with dowel hole 26 and tab notch 28 in blade shank 24, for properly aligning blade 20 with guide 32. As will become apparent, blade 20 may be placed on plate 56 so that edge 22 (FIG. 3) may be facing upwardly or downwardly to provide cutting in either direction depending on the blade position.

Affixed as by welding to the upper surface of guide shank 54 is tubular section 62. Affixed as by welding to guide 32 along line 64 is strengthening rib 66. Rib 66 extends orthogonally from the upper surface of guide 32. Also, rib 66 is welded, or otherwise secured, at points 68 and 69 to tubular section 62. As will become apparent, rib 66 provides a visual indication of the attitude of guide 32 and knife 20.

Handle 70 is an elongated tubular section having an axis which is vertically offset from, and is inclined relatively to the longitudinal axis of guide 32. Slots 72, one on either side of handle 70, are cut in handle 70 to receive the tubular wall of section 62. Slots 72 are welded or otherwise suitably secured to section 62.

Dowel hole 26 and tab notch 28 in blade 20 are placed over dowel 58 and tab 60 to properly key blade 20 to guide 34. Blade shank 24 may be placed on spacer plate 56 so that edge 22 is facing upwardly or downwardly (FIG. 3), depending on the direction of cut that is desired. Once shank 24 has been placed on spacer plate 56, a band clamp 80 having an elongated band 82 with longitudinally spaced transverse arcuate openings 84 therein, is placed around tubular section 62 and in contact with the lower surface of shank 24. Band 80 is of a kind well known to the art and one that is widely available. The free end of band 82 is inserted into engagement with a thumb screw 86 which is rotatably mounted in screw housing 88. The spiral threads on screw 86 register with the openings 84, and upon rotation of screw 86, openings 84 are sequentially engaged by the spirals to tighten band 84 on section 62 clamping securely knife 20 to spacer plate 56. The thumb screw 86 has rounded edges 90 to prevent cutting the operator's or surgeon's sterile gloves during cutting blade 20 assembly or skin flap creation.

Guide surface 34 is slightly inclined and in the assembled position, FIG. 3, diverges from blade 20. Guide surface 34 is adapted to be pressed against the outer skin and due to the divergency between surface 34 and blade 20, the skin flap is tapered in thickness and, as is known in the art, this will aid in supplying the prepared skin with adequate nourishment during the operation and during the healing period thereafter. Typically, the distance between blade 20 and guide 34 increases from approximately 2 millimeters at the edge 36 of guide surface 34 to 6 millimeters at point 30 of knife 20. The distance between edge 36 and point 30 is typically 80 millimeters.

Tip 50 of guide 32 is substantially aligned, in the longitudinal direction, with point 30 of knife 20. Therefore, the surgeon has a visual indication from the top of guide 32 of the location of point 30. Also, regardless of which position knife blade 20 is inserted against spacer plate 56, either edge 44 or edge 46 will be parallel to the cutting edge 22. Thus, the same relative position between cutting edge 22 and guide edge 44 or 46 is obtained in either blade position. Also, the guide edge 38 extends beyond point 30 of the knife 20 protecting it against damage.

FIG. 6 is an alternative embodiment of this invention showing a guide surface 34a having a longitudinal channel 92 which has a curvilinear cross section as shown. This surface permits a certain amount of skin accumulation during the cutting action to provide a desired flap cut.

The transverse dimension of guide surface 34, FIG. 3, is approximately three times the transverse dimension of the knife blade 20 which is disposed substantially centrally of guide surface 34. Thus, the portions of said guide surface 34 that extend laterally beyond the blade 20 may be characterized as guide surface extensions which resist tilting of the blade 20 about its longitudinal axis when the latter is inserted into the flesh with the guide surface 34 flat against the skin. Due to this greater dimension, more balanced uniform surgical manipulation is provided as well as a better indication of the "attack angle" or attitude of blade 20. In addition, the provision of support rib 66 aids in determining this attitude. For example, if rib 66 is vertical and appears as an edge to a surgeon directly above the knife, (FIG. 1), surface 34 and blade 20 are approximately horizontal. However, if either side of rib 66 is viewable, then surface 34 is tilted; the amount of side viewable corresponds to the amount of tilt and the side that is viewable indicates the direction of tilt.

By altering the attitude, a slightly thicker or a thinner flap section may be prepared as desired by the surgeon without the need of a different guide plate.

Due to the location and inclination of handle 70, a surgeon's hand may easily grasp the surgical knife and still provide adequate clearance over the body surface and any clamps that may be thereon. Use of an instrument permitting manual operation offers greatly improved surgical control, minimizing unnecessary tissue damage and bleeding, and resulting in necrosis of the tissue. The versatility of the surgical knife of this invention permits the surgeon to become completely familiar with a single instrument for doing numerous tasks building surgeon confidence and capability. Use of a manual knife as opposed to a power operated knife greatly reduces the complexity and expense, is more reliable, and improves flexibility of use due to the absence of a relatively bulky instrument which is cable connected to a power source greatly restricting the surgeon's freedom of movement.

Clamp 82 is hand-operated, being removable with thumb screw 86 making unnecessary any tools for removal, and presents a substantially flush surface on the bottom of knife 20 which is against the body surface (FIG. 2). Knife 20 may be turned 180° to change the cutting direction readily and quickly. Due to the symmetry of construction, the instrument may be used equally well by right and left handed surgeons. Dowel 58 and tab 60 are placed on the longitudinal axis of guide 32 and dowel hole 26 and tab notch 24 are placed on the longitudinal axis of blade 20 whereby when the blade 20 is turned over (rotated at 180° on its longitudinal axis), the cutting edge 22 will be at the same relative position to edge 44 or edge 46. Due to the clearance provided by the handle position, any skin clamps are not moved to overextend or stretch the skin while the flap is being cut thereby minimizing any unneccessary tissue damage and bleeding. Extention of guide end 38 beyond knife point 30 provides protection against accidental cutting and further minimizes damage to the blade point. The instrument thus shown is light in weight and comparatively inexpensive and yet providing a manual tool of greater use resulting in increased surgical proficiency.

Following is listed values of the various components of a working embodiment of this invention, these values being given as exemplary only and not to be considered as limitative of the invention:

Dimensions of a blade and guide, which dimensions are lettered in FIGS. 2 and 3 are as follows:

| | | |
|---|---|---|
| Blade 20 length | a = 3.150" | spacing h = .0236" |
| Blade 20 width | b = .625" | spacing i = .0079" |
| | c = .500" | |
| | c' = .5625" | |
| guide 34 length | d = 3.75" | |
| guide 34 width | e = 1.4375" | |
| | f = 1.125" | |
| | g = 1.250" | |
| shank height | j = 1.375" | |
| handle 70 diameter | = 1.00" | |

While there have been described above the principles of this invention in connection with specific apparatus, it is to be clearly understood that this description is made only by way of example and not as a limitation to the scope of the invention.

What is claimed is:

1. A surgical knife assembly comprising:

a handle portion;

an elongated knife blade having a cutting edge and a transversely spaced opposite edge; said knife blade being secured at its base end to said handle portion;

an elongated blade guide secured at a base end to said handle portion in overlying spaced relation to said blade and having a surface portion overlying said blade in substantial parallelism therewith and defining a cutting clearance therebetween;

said blade guide having a transverse dimension greater than the transverse dimension of said knife blade;

said blade guide extending transversely beyond the opposite edges of said blade, respectively, a distance to resist tilting of the blade about its longitudinal axis when the latter is inserted into the flesh in a position which disposes the blade guide surface portion in flat engagement with a patient's skin;

said guide having a base edge, a distal edge and two side edges, said side edges being substantially longer than said distal and base edges, said guide being tapered from said base edge to said distal edge with one side edge being substantially parallel to said cutting edge, said side edges and said distal edge being arcuately formed to provide a rounded edge surface extending away from the plane of said knife blade; and a guide shank on said base edge and extending longitudinally therefrom.

2. A surgical knife assembly according to claim 1 with:

a spacer plate being affixed to said guide shank;

said plate having a dowel and tab extending orthogonally therefrom on the longitudinal axis of said guide;

said blade base end having a blade shank affixed to and extending longitudinally therefrom;

said blade shank having a dowel hole and a tab notch formed therein and longitudinally spaced along the longitudinal axis of said blade and registrable with and placeable over the dowel and tab on said guide shank, respectively;

said releasable securing means clamping said blade shank to said guide shank; and a portion of said releaseable securing means being substantially flush with said blade thereby providing for unobstructed movement of said knife.

3. A surgical knife assembly according to claim 1 with:

an elongated handle being attached to said guide shank; and said handle being offset in a direction away from the plane of said guide and inclined in a direction away from the plane of said guide to provide hand clearance during manipulation of said knife.

4. A surgical knife assembly comprising:

a handle portion;

an elongated knife blade having a cutting edge and a transversely spaced opposite edge; said knife blade being secured at its base end to said handle portion;

an elongated blade guide secured at a base end to said handle portion in overlying spaced relation to said blade and having a surface portion overlying said blade in substantial parallelism therewith and defining a cutting clearance therebetween;

said blade guide having a transverse dimension greater than the transverse dimension of said knife blade;

said blade guide extending transversely beyond the opposite edges of said blade, respectively, a distance to resist tilting of the blade about its longitudinal axis when the latter is inserted into the flesh in a position which disposes the blade guide surface portion in flat engagement with the patient's skin, said guide plate having a distal end from said base end, said distal end turned reversely toward said base end so that the tip of said distal end overlies the guide surface opposite to said surface portion;

said blade having a distal end spaced from the blade end; and said tip substantially overlying said blade distal end thereby providing a visual indication of said blade distal end.

5. A surgical knife assembly comprising:

a handle portion;

an elongated knife blade having a cutting edge and a transversely spaced opposite edge; said knife blade being secured at its base end to said handle portion;

an elongated blade guide secured at a base end to said handle portion in overlying spaced relation to said blade and having a surface portion overlying said blade in substantial parallelism therewith and defining a cutting clearance therebetween;

said blade guide having a transverse dimension greater than the transverse dimension of said knife blade;

said blade guide extending transversely beyond the opposite edges of said blade, respectively, a distance to resist tilting of the blade about its longitudinal axis when the latter is inserted into the flesh in a position which disposes the blade guide surface portion in flat engagement with a patient's skin, the edge portions of said blade guide opposite the edges of said knife blade being upturned from the plane of said knife blade, said upturned edges being in the form of curved surfaces, the distal end of said blade guide also having an upwardly curved edge portion that merges with the other upturned edges.

6. The knife assembly of claim 5 wherein said blade guide surface portion is flat with the exception of the upturned edges, said handle portion being offset in a direction away from said blade guide thereby to provide hand clearance during manipulation of the knife assembly.

7. The knife assembly of claim 6 wherein the width of the flat portion of said guide plate is more than twice the width of the knife blade.

* * * * *